United States Patent [19]

Gössel et al.

[11] Patent Number: 4,814,518

[45] Date of Patent: Mar. 21, 1989

[54] PROCESS FOR EXTRACTING NITROHYDROXYAROMATICS FROM AQUEOUS SOLUTIONS

[75] Inventors: Helmut Gössel, Frankfurt am Main; Herbert Kuckertz, Kelkheim; Siegbert Rittner, Mörfelden-Walldorf; Josef Rosenfelder, Hofheim am Taunus; Bernhard Wojtech, Bad Soden am Taunus, all of Fed. Rep. of Germany

[73] Assignee: Hoechst Aktiengesellschaft, Frankfurt am Main, Fed. Rep. of Germany

[21] Appl. No.: 84,483

[22] Filed: Aug. 12, 1987

[30] Foreign Application Priority Data

Aug. 14, 1986 [DE] Fed. Rep. of Germany ....... 3627653

[51] Int. Cl.[4] ...................... C07C 79/22; C07C 37/68
[52] U.S. Cl. .................................. 568/708; 568/706; 568/712; 568/757
[58] Field of Search ............... 568/706, 708, 757, 712

[56] References Cited

U.S. PATENT DOCUMENTS

| | | | |
|---|---|---|---|
| 3,597,351 | 8/1971 | Landenburg et al. | 568/708 |
| 4,418,221 | 11/1983 | Yasuda et al. | 568/757 |
| 4,626,605 | 12/1986 | Wojtech et al. | |

FOREIGN PATENT DOCUMENTS

| | | | |
|---|---|---|---|
| 406150 | 11/1924 | Fed. Rep. of Germany . | |
| 3436349 | 4/1986 | Fed. Rep. of Germany . | |
| 21352 | 9/1964 | Japan | 568/757 |
| 0032749 | 2/1985 | Japan | 568/708 |
| 2095253 | 9/1982 | United Kingdom | 568/757 |

OTHER PUBLICATIONS

*Winnacker–Kucher Chemische Technologie,* 4th Ed., vol. 6 (Organic Technolgy II), ed. Harnisch et al., Carl Hanser Verlag, Munich, 1982, pp. 173–174.

*Primary Examiner*—Werren B. Lone

[57] ABSTRACT

The invention relates to a process for extracting nitrohydroxyaromatics from aqueous solutions. In this process, the extracting agent used is an amine salt which comprises an aliphatic amine having a total carbon number of 10 to 75 and a strong acid. The amine salt can be employed undiluted or diluted with an organic solvent.

16 Claims, No Drawings

PROCESS FOR EXTRACTING NITROHYDROXYAROMATICS FROM AQUEOUS SOLUTIONS

The invention relates to a process for extracting nitrohydroxyaromatics from aqueous solutions.

It is known that, in the preparation of nitrohydroxyaromatic compounds, large amounts of waste water are produced which can only be purified with great difficulty. Nitrohydroxyaromatics are toxic and, in addition, the majority are poorly biodegradable, so that the disposal of such waste water is subject to strict official regulations. According to the current state of the art, nitrohydroxyaromatic waste water is usually subjected, before biological purification, to prepurification in order to reduce the concentration and thus to lessen the danger that microorganisms involved in the biological purification are destroyed. Hitherto, besides oxidation and reduction processes, many methods which work on the principles of thermal separation processes, such as, for example, adsorption on charcoal, have been proposed for the prepurification (Winnacker-Küchler, Chemische Technologie [Chemical Technology], 4th edition, volume 6, 1982, p. 173).

Oxidation and reduction processes, in which, for example, oxidation is carried out using ozone or reduction is carried out using hydrogen in the presence of noble metal catalysts, are extremely complicated chemical processes. They require auxiliary chemicals and lead to losses, since recovery of the nitrohydroxyaromatics is no longer possible as a result of chemical degradation.

Charcoal adsorption processes likewise have weaknesses. Thus, they can only be used, for example, for dilute nitrohydroxyaromatic waste water. Relatively high contents of inorganic salts in the waste water, which lead to clogging of the activated charcoal pores, are also detrimental here. Charcoal adsorption generally follows a regenerative process step, which must usually be carried out thermally and therefore involves complicated equipment.

German Offenlegungsschrift No. 3,436,349 has already disclosed that phenols, which, as is known, have a weakly acidic or neutral reaction, are oxidation-sensitive and sometimes have a reducing effect, can be extracted with the aid of salts of higher amines.

Surprisingly, it has now been found that strongly acidic and oxidizing nitrohydroxyaromatics can be extracted from waste water, even virtually completely, when such salts are used as extracting agents. The invention therefore relates to a process for extracting nitrohydroxyaromatics from aqueous solutions, which comprises using as extracting agent an amine salt consisting of an aliphatic amine having a total carbon number of 10 to 75 and a strong acid, it being possible for the amine salt to be employed undiluted or diluted with an organic solvent.

The amine salt is either prepared separately and then added to the waste water, or is formed in situ. For in situ formation, only the amine is generally added if the waste water already contains sufficient acid, otherwise the amine and an acid are added.

The aliphatic amines on which the amine salts are based and which may be primary, secondary or tertiary should have a total carbon number of 10 to 75, preferably 20 to 50 carbon atoms, and may be straight-chain, cyclic or branched. Of the amines mentioned, tertiary amines, above all tri-n-octylamine, tri-isooctylamine, tri-n-decylamine, tri-isodecylamine, tri-n-dodecylamine, tri-isododecylamine, and mixtures thereof, are particularly preferred due to their low chemical reactivity.

Strong acids which are particularly suitable for amine salt formation are mineral acids, such as phosphoric acid, nitric acid, hydrochloric acid or sulfuric acid, above all hydrochloric acid or sulfuric acid.

The amine salt forms rapidly and quantitatively on mixing the water-insoluble amine and acidic waste water, the acid passing over into the organic phase from the aqueous phase with formation of an ion pair. The equilibrium of this "neutralization" is right over to the side of the amine salt. The equilibrium constants are $10^4$ to $10^8$, depending on the amine and the acids. Such amine salts have the composition $(RH_2NH)X$, $(R_2HNH)X$ or $(R_3NH)X$, where X is the anion of the acid.

If the amine salts are prepared separately, they can be added undiluted to the waste water, but, in order to reduce the viscosity, they may alternatively be diluted with an organic solvent, for example a hydrocarbon. Partial conversion of the amine into the amine salt is also possible, the remaining (free) amine acting as a diluent. In the in situ formation of the amine salts, an organic solvent may analogously be present.

Using the amine salts mentioned, nitrohydroxyaromatics of the general formula (I) can be removed:

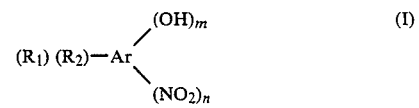

In the formula (I), $R_1$ and $R_2$ denote hydrogen, fluorine, chlorine, bromine, or a methyl, trifluoromethyl, ethyl, propyl, i-propyl, n-butyl or sec.-butyl radical. Ar is a benzene or naphthalene radical, and m and n are 1, 2 or 3.

The following may be mentioned as examples: 2-nitrophenol, 3-nitrophenol, 4-nitrophenol, 2-nitro-1-naphthol, 4-nitro-1-naphthol, 1-nitro-2-naphthol, 2-chloro-3-nitrophenol, 2-chloro-4-nitrophenol, 2-chloro-5-nitrophenol, 3-chloro-2-nitrophenol, 3-chloro-4-nitrophenol, 3-chloro-5-nitrophenol, 4-chloro-2-nitrophenol, 4-chloro-3-nitrophenol, 5-chloro-2-nitrophenol, 6-chloro-2-nitrophenol, 2,6-dichloro-4-nitrophenol, 4,6-dichloro-2-nitrophenol, 3-nitro-o-cresol, 4-nitro-o-cresol, 5-nitro-o-cresol, 6-nitro-o-cresol, 2-nitro-m-cresol, 4-nitro-m-cresol, 5-nitro-m-cresol, 6-nitro-m-cresol, 2-nitro-p-cresol, 3-nitro-p-cresol, 2,4,6-trinitro-m-cresol, 2,3,6-trichloro-6-nitrophenol, 2,4-dibromo-6-nitrophenol, 2,6-dibromo-4-nitrophenol, 3-trifluoromethyl-4-nitrophenol, 4-trifluoromethyl-2-nitrophenol, 4-trifluoromethyl-2,6-dinitrophenol, 4-trifluoromethyl-3-chloro-2,6-dinitrophenol, 2,3-dinitrophenol, 2,4-dinitrophenol, 2,5-dinitrophenol, 2,6-dinitrophenol, 2,4-/2,6-dinitrophenol mixtures, 3,4-dinitrophenol, 3,5-dinitrophenol, 2,4-dinitroresorcinol, 3,5-dinitroresorcinol, dinitro-o-cresol (=2-hydroxy-3,5-dinitrotoluene), dinitro-sec.-butylphenol (=2-hydroxy-3,5-dinitrobutylbenzene) and 1,3,5-trinitrophenol.

The concentration in the aqueous phase of the nitrohydroxyaromatics to be extracted can extend up to the saturation concentration. The aqueous solutions may also contain other dissolved organic or inorganic compounds and suspended particles, so long as these do not interfere with the extraction. The process also permits the extraction of nitrohydroxyaromatics from very dilute solutions.

The great advantage of the process according to the invention is not only its broad field of application, but, above all, its extremely purifying effect, which is expressed in partition coefficients up to more than 10,000. It is thereby possible to purify unpurified waste water in just one step, i.e. by simply stirring once with the extracting agent, to a few ppm or below into the ppb region. However, the extraction expense is so low not just due to the one-step procedure; the high extraction capacity also allows very small amounts of extracting agent to suffice, so that the waste water/extracting agent phase volume ratio can be set up to 20:1. In the case of a multistep procedure, even higher values are possible. Single-step extraction by stirring can be carried out batchwise or (advantageously) continuously. If the extraction is carried out in a multistep manner in a crosscurrent or continuously in a countercurrent, the ppb region is reached without difficulty, even in the case of relatively high concentrations of nitrohydroxyaromatics in the waste water.

Another advantage of the process according to the invention is removal of mineral acid, besides removal of nitrohydroxyaromatics, in mineral acid-containing waste water, the acid passing over from the waste water into the amine phase with formation of the extraction-effective amine salt.

A further advantage of the process according to the invention is the possibility of simple recovery of the amine from the extract by single-step back-extraction with sodium hydroxide solution. During this, the nitrohydroxyaromatics, together with the mineral acid bound to the amine, pass quantitatively into the aqueous NaOH phase as sodium salts, whereas the free amine remains in the organic phase and can be fed back into the waste water extraction. Amine recovery can likewise be achieved in one step by simple stirring if an amount of NaOH equivalent to the content of mineral acid+nitrohydroxyaromatic is employed. Concentrated sodium hydroxide solution in an equivalent amount is preferably used, since a particularly high concentration of the nitrohydroxyaromatics in the back-extract can then be achieved. After concentration in the back-extract, which can be one to two powers of ten, the nitrohydroxyaromatics can be recovered, either as salts or, after acidification, in the hydroxy form in which case the majority of them precipitate and can be filtered off. In this manner, a virtually loss-free procedure is guaranteed.

The invention will be illustrated with reference to the following examples. In these, the extractions were always carried out at room temperature. The name Hostarex A 327 (protected as a trade mark in the Federal Republic of Germany) denotes a mixture of equal parts of tri-n-octylamine and tri-n-decylamine.

COMPARISON EXAMPLE 1000 ml of an aqueous 0.50 percent strength by weight 4-nitrophenol solution were equilibrated with 100 ml (80.6 g) of Hostarex A 327 in a shaking cylinder, and the phases were analyzed after separation. The aqueous phase (995.7 g) had a concentration of 576 ppm of 4-nitrophenol, and the extracted (amine) phase (84.9 g) had a concentration of 5.21% by weight of 4-nitrophenol. This gives a partition coefficient D (=ratio of the concentration in the organic phase to the aqueous phase) of 90.5.

EXAMPLE 1

1000 ml of the same aqueous solution as in the comparison example, containing 0.50% by weight of 4-nitrophenol, were firstly treated with 22 g of concentrated hydrochloric acid (0.80% by weight in the solution) and then equilibrated as in the comparison example with 100 ml (80.6 g) of Hostarex A 327. The aqueous phase (1003.4 g) only contained 7.6 ppm of 4-nitrophenol, but, in contrast, the amine phase (99.2 g) contained 5.035% by weight. This corresponds to a partition coefficient (D) of 6625.

EXAMPLE 2

The purifying action of various amines was investigated using samples of a waste water containing 0.702% by weight of 4-nitrophenol and 1.4% by weight of hydrochloric acid. To this purpose, the distribution equilibria were determined by extracting by stirring in a stirred vessel, in each case at a waste water:amine ratio by volume of 10:1. The following extracting agents were employed:

A: Hostarex A 327
B: Tri-isooctylamine (=Hostarex A 324, protected as a trade mark in the Federal Republic of Germany)
C: Di-2-ethylhexylamine Table 1 below shows the equilibrium concentrations in individual phases along with the corresponding partition coefficients (D) and extraction yields:

TABLE 1

| Extracting agent | 4-Nitrophenol concentration | | D | Extraction yield, % |
|---|---|---|---|---|
| | Amine phase % by weight | Waste water phase ppm | | |
| A | 7.195 | 6.6 | 10,902 | 99.99 |
| B | 6.975 | 7.1 | 9,824 | 99.98 |
| C | 6.840 | 48.4 | 1,413 | 99.93 |

EXAMPLE 3

1000 g of Hostarex A 327 were brought into contact with 443.5 ml of 4 N sulfuric acid by means of vigorous stirring. During this, the sulfuric acid passed quantitatively from the aqueous phase into the organic amine phase, so that it was converted to 70% into the amine sulfate $(R_3NH)_2SO_4$. After separating off the aqueous phase, this amine sulfate/amine mixture was employed as extracting agent in order to remove nitrophenol from an aqueous solution which, apart from 0.50% by weight of 4-nitrophenol, contains no further components. At a waste water:extracting agent phase volume ratio of 10:1, the following phase concentrations of 4-nitrophenol were obtained by single-step extraction by stirring in a stirred vessel: extracted (amine) phase 5.458% by weight, aqueous phase 4.5 ppm. This corresponds to a partition coefficient of 12,130 and an extraction yield of 99.91%.

EXAMPLE 4

The extraction behavior of amines which were diluted by solvents was determined. To this purpose, Hostarex A 327 was diluted once with n-dodecane and once with ®Solvesso 150 ($C_{10}$-$C_{11}$alkylbenzenes) to form a 40% strength by weight amine solution (=extracting agent). The waste water contained 0.556% by weight of 4-nitrophenol and 1.32% by weight of hydrochloric acid. The equilibrium was produced in one step in a stirred vessel at a waste water:extracting agent phase volume ratio 4:1. Table 2 below shows the results.

TABLE 2

| Extraction agent | 4-Nitrophenol concentration | | D | Extraction yield, % |
| --- | --- | --- | --- | --- |
| | Amine phase % by weight | Waste water phase, ppm | | |
| 40% by weight of Hostarex A 327 in n-dodecane | 2.886 | 8.5 | 3,400 | 99.85 |
| 40% by weight of Hostarex A 327 in Solvesso 150 | 2.522 | 4.8 | 5,250 | 99.91 |

EXAMPLE 5

A waste water containing 0.702% by weight of 4-nitrophenol and 1.4% by weight of hydrochloric acid was purified in a 3-step crosscurrent extraction with Hostarex A 327 at a waste water:amine phase volume ratio of 20:1 in each step. The 4-nitrophenol concentration in the waste water was 19.1 ppm after the 1st step, 0.7 ppm after the 2nd step and less than 0.1 ppm after the 3rd step.

EXAMPLE 6

The same waste water as in Example 4 was purified in one step in a stirred vessel using Hostarex A 327 at a waste water:amine phase volume ratio of 10:1 (1000 ml:100 ml). The extract (102.2 g) contained 7.19% by weight of 4-nitrophenol, and purified waste water (1025.6 g) contained 7 ppm of 4-nitrophenol. This corresponds to an extraction yield of 99.9%. After separating the phase the extract was extracted by stirring in one step with 56 g of 15% strength sodium hydroxide solution for the back-extraction. During this, the 4-nitrophenol and the hydrochloric acid bound to the amine pass completely as Na salts into the sodium hydroxide solution phase, whereas the regenerated and purified Hostarex A 327 was fed back into the extraction.

EXAMPLE 7

A waste water containing 0.179% by weight of 2-nitrophenol and 0.742% by weight of hydrochloric acid was extracted by stirring in one step in a stirred vessel until the equilibrium was produced with Hostarex A 327 in the waste water:amine ratio by volume of 10:1 (600 ml:60 ml). The extract (56.36 g) had a concentration of 2.019% by weight of 2-nitrophenol, and the waste water raffinate (629.8 g) had a concentration of 6.4 ppm of 2-nitrophenol. This corresponds to a partition coefficient of 3,150 and an extraction yield of 99.65%. The back-extraction was carried out in one step by stirring the extract with 33 g of 15% strength sodium hydroxide solution. During this, 2-nitrophenol and the hydrochloric acid bound to the amine passed completely as sodium salts into the sodium hydroxide solution phase. The regenerated and purified Hostarex A 327 was fed back into the extraction.

EXAMPLE 8

A waste water containing 307 ppm of 2,4-dinitrophenol and 1.5% of hydrochloric acid was extracted in one step by stirring with Hostarex A 327 in the waste water:amine ratio by volume of 20:1 (600 ml:30 ml) until equilibrium was produced. The extract (29.5 g) contained 0.650% by weight of 2,4-dinitrophenol, and the waste water raffinate (618.7 g) contained 0.5 ppm of 2,4-dinitrophenol. This corresponds to a partition coefficient of 13,000 and an extraction yield of 99.98%. The dinitrophenol and the hydrochloric acid were removed completely from the extract by means of a single-step back-extraction with 10 g of 25% strength sodium hydroxide solution.

EXAMPLE 9

A waste water containing 180 ppm of 4-chloro-2-nitrophenol and 0.86% by weight of hydrochloric acid was extracted in one step by stirring with Hostarex A 327 in the waste water:amine ratio by volume of 10:1 (650 ml: 65 ml) until equilibrium was produced. The extract (60.4 g) contained 0.196% by weight of 4-chloro-2-nitrophenol, and the waste water raffinate (650.0 g) contained 0.2 ppm of 4-chloro-2-nitrophenol. This corresponds to a partition coefficient of 9,800 and an extraction yield of 99.89%. 22 g of a 25% strength sodium hydroxide solution were required for complete back-extraction by single-step stirring.

EXAMPLE 10

A waste water containing 394 ppm of 4-methyl-2-nitrophenol and 1.12% by weight of hydrochloric acid was extracted in one step with stirring with Hostarex A 327 in the waste water:amine ratio by volume of 10:1 (600 ml:60 ml) until equilibrium was produced. The extract (55.52 g) contained 0.431% by weight of 4-methyl-2-nitrophenol, and the waste water raffinate (603.24 g) contained 2.3 ppm of 4-methyl-2-nitrophenol. This corresponds to a partition coefficient of 1,874 and an extraction yield of 99.42%. 33 g of a 15% strength sodium hydroxide solution were required for complete back-extraction by stirring in two steps.

EXAMPLE 11

A waste water containing 0.297% by weight of 3-trifluoromethyl-4-nitrophenol and 1.3% by weight of hydrochloric acid was extracted in one step by stirring with Hostarex A 327 in the waste water:amine ratio by volume of 10:1 (600 ml:60 ml) until equilibrium was produced. The extract (58.82 g) contained 3.069% by weight of 3-trifluoro-methyl-4-nitrophenol, and the waste water raffinate (597.31 g) contained 0.2 ppm of 3-trifluoromethyl-4-nitrophenol. This corresponds to a partition coefficient of 153,400 and an extraction yield of greater than 99.99%. 35 g of a 15% strength sodium hydroxide solution were required for complete back-extraction by single-step stirring.

EXAMPLE 12

A waste water containing 0.150% by weight of 2,4,6-tri-nitrophenol (picric acid) and 1.3% by weight of hydrochloric acid was extracted in one step by stirring with Hostarex A 327 in the waste water:amine ratio by volume of 10:1 (1000 ml:100 ml) until equilibrium was produced. The extract (99.21 g) contained 1.529% by weight of picric acid, and the waste water raffinate (992.7 g) contained 0.3 ppm of picric acid. This corresponds to a partition coefficient of 50,970 and an extraction yield of 99.98%. 56 g of a 15% strength sodium hydroxide solution were required for complete back-extraction by single-step stirring.

We claim:

1. A process for removing a nitrohydroxyaromatic compound from an aqueous solution, said aqueous solution containing a nitrohydroxyaromatic of the formula:

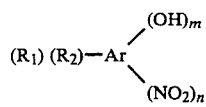

wherein:
$R_1$ and $R_2$ denote hydrogen, fluorine, chlorine, bromine, methyl, trifluoromethyl, ethyl, propyl, i-propyl, n-butyl, or sec.-butyl; Ar is a benzene or naphthalene radical; and m and n are 1, 2 or 3;

said process comprising the step of extracting the nitrohydroxyaromatic compound or compounds with an organic phase comprising an aliphatic amine salt of a strong acid, the aliphatic amine salt having a total carbon number of 10 to 75, and separating the resulting aqueous phase which is substantially free of nitrohydroxyaromatic compounds.

2. The process as claimed in claim 1, wherein the aliphatic amine salt is a salt of a tertiary amine.

3. The process as claimed in claim 1, wherein the strong acid from which the aliphatic amine salt is derived is hydrochloric or sulfuric acid.

4. The process as claimed in claim 1, wherein the organic phase comprising the aliphatic amine salt contains an organic solvent for diluting the aliphatic amine salt.

5. The process as claimed in claim 1, wherein the organic phase consists essentially of undiluted aliphatic amine salt of a strong acid.

6. The process as claimed in claim 1, wherein the strong acid from which the aliphatic amine salt is derived is a mineral acid.

7. The process as claimed in claim 1, wherein said aqueous solution is acidic, and the aliphatic amine salt is formed in situ.

8. The process as claimed in claim 1, which comprises the further step of recovering the nitrohydroxyaromatics from the organic phase by back-extracting with aqueous NaOH.

9. The process as claimed in claim 1, wherein the total number of carbon atoms in the aliphatic amine of the aliphatic amine salt is 20 to 50.

10. The process as claimed in claim 9, wherein the aliphatic amine comprises trioctyl amine, tridecylamine or mixtures thereof.

11. The process as claimed in claim 1, wherein the aqueous solution is waste water from the production of the nitrohydroxyaromatics.

12. The process as claimed in claim 1, wherein the organic phase comprising the aliphatic amine salt and the strong acid is selected such that, after extraction, the ratio of the concentration of nitrohydroxyaromatic compound in said organic phase to the concentration of nitrohydroxyaromatic compound in the separated aqueous phase is at least about 1,400.

13. The process as claimed in claim 1, wherein the aliphatic amine salt is a salt of a tertiary amine having a total of 20 to 50 carbon atoms and the strong acid is a mineral acid.

14. The process as claimed in claim 1, which comprises the further step of separating after extraction the organic phase into (a) the sodium salts of the nitrohydroxyaromatic compound and the strong acid and (b) the aliphatic amine, by back-extracting with aqueous NaOH.

15. The process as claimed in claim 1, wherein the volume ratio of said organic phase to the aqueous phase, during extraction, is at least about 10:1.

16. A process for removing nitrohydroxyaromatics from aqueous solutions containing the nitrohydroxyaromatics, which comprises the step of extracting the nitrohydroxyaromatics with an organic phase comprising an aliphatic amine salt of a strong acid, the aliphatic amine of the amine salt having a total carbon number of 10 to 75.

* * * * *